US00PP22029P2

(12) United States Plant Patent
Pierce

(10) Patent No.: US PP22,029 P2
(45) Date of Patent: Jul. 12, 2011

(54) ***CALIBRACHOA* PLANT NAMED 'CAL ORNGISE'**

(50) Latin Name: ***Calibrachoa* sp.**
Varietal Denomination: Cal Orngise

(75) Inventor: Robert O. Pierce, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/804,406

(22) Filed: Jul. 21, 2010

(51) Int. Cl.
*A01H 5/00* (2006.01)

(52) U.S. Cl. ..... Plt./413

(58) Field of Classification Search ..... Plt./413
See application file for complete search history.

*Primary Examiner* — Kent L Bell
(74) *Attorney, Agent, or Firm* — S. Matthew Edwards

(57) ABSTRACT

A new *Calibrachoa* plant named 'Cal Omgise' particularly distinguished by the medium sized, variegated orange and yellow flowers, deep green foliage, initially mounding then more spreading and decumbent plant habit with vigorous growth.

1 Drawing Sheet

Latin name of the genus and species of the plant claimed: *Calibrachoa* sp.

Varietal denomination: 'Cal Orngise'.

BACKGROUND OF THE NEW PLANT

The present invention comprises a new *Calibrachoa*, botanically known as *Calibrachoa* sp. and hereinafter referred to by the variety name 'Cal Orngise'.

'Cal Orngise' is a product of a planned breeding program. The new cultivar has medium sized, variegated orange and yellow flowers, deep green foliage, initially mounding then more spreading and decumbent plant habit, with vigorous growth.

'Cal Omgise' originated from a hybridization made in October 2006 in a controlled breeding program in Gilroy, Calif., USA. The female parent was the unpatented, proprietary plant designated as '1511-1', having apricot flower color, later flowering and less vigor.

The male parent of 'Cal Omgise' was the unpatented, proprietary plant designated as '717-1' with light orange flower color, smaller flowers and lighter foliage. The resultant seed was sown in January 2007.

'Cal Omgise' was selected as one flowering plant within the progeny of the stated cross in April 2007 in a controlled environment in Gilroy, Calif. USA.

The first act of asexual reproduction of 'Cal Orngise' was accomplished when vegetative cuttings were propagated from the initial selection in April 2007 in a controlled environment in Gilroy, Calif. USA.

BRIEF SUMMARY OF INVENTION

Horticultural examination of plants grown from cuttings of the plant initiated in April 2007 in Gilroy, Calif., and continuing thereafter, has demonstrated that the combination of characteristics as herein disclosed for 'Cal Orngise' are firmly fixed and are retained through successive generations of asexual reproduction.

'Cal Orngise' has not been observed under all possible environmental conditions. The phenotype may vary significantly with variations in environment such as temperature, light intensity and day length.

Plant Breeder's Rights for this cultivar were applied for in Canada on Feb. 15, 2010 (#10-6840), in CVPO on Mar. 15, 2010 (#2010/0644), and in Switzerland on Nov. 19, 2009 (#09-2629). 'Cal Orngise' has not been made publicly available more than one year prior to the filing of this application.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

The accompanying photographic drawing shows typical flower and foliage characteristics of 'Cal Orngise' with colors being as true as possible with an illustration of this type. The photographic drawing shows a flowering potted plant of the new variety and a close-up of the flowers.

DETAILED BOTANICAL DESCRIPTION

The aforementioned photographs were taken in April 2010 from plants growing in a greenhouse trial in Gilroy, Calif. USA. These plants were growing in 4 inch pots and were approximately 15-16 weeks of age.

The plant descriptions and measurements were taken in mid-May 2010, in Hillscheid, Germany on 9 week old plants that had been planted into 12 cm pots in mid-March and were grown without pinching, on benches in a greenhouse at a minimum temperature (heating temperature) of 12° C.

Color Chart used: Royal Horticultural Society Colour Chart (R.H.S.) 2001

TABLE 1

DIFFERENCES BETWEEN THE NEW VARIETY 'CAL ORNGISE' AND A SIMILAR VARIETY

| | 'Cal Orngise' | 'Cal Sunre' (U.S. Plant Pat. No. 14,605) |
|---|---|---|
| Flower color: | RHS 13A with RHS 32B lines; or RHS 35A, with fine yellow stripes of RHS 16A; and with narrowish reddish ring of RHS 46B near the bottom portion of corolla opening. | RHS 9A and RHS 33A |
| Flower diameter: | Larger | Smaller |
| Pedicel length: | Longer | Shorter |
| Branching habit: | More branches | Fewer branches |

Plant:

*Form, growth and habit.*—Initially mounding, then more spreading and decumbent, pinching enhances the number of branches.

*Plant height.*—6.5-10.0 cm.

*Plant height (inflorescence included).*—7.5-12.0 cm.

*Plant width.*—32-40 cm.

*Quantity of main branches.*—10-18.

*Quantity of secondary branches.*—3-4 per basal branch.

*Time to produce a flowering plant.*—About 8-10 weeks for a 12 cm pot.

Roots:

*Number of days to initiate and produce a rooted cutting.*—25-28 days at 22° C.

*Type.*—Fibrous.

*Color.*—RHS 158D.

Foliage:

*Arrangement.*—Alternate.

*Immature leaf, color of upper surface.*—RHS 137C.

*Immature leaf, color of lower surface.*—RHS 138A to RHS 138B.

*Mature leaf, color of upper surface.*—RHS 137A to nearly RHS 147A.

*Mature leaf, color of lower surface.*—RHS 137C.

*Length.*—3.0-3.8 cm.

*Width.*—1.6-2.0 cm.

*Shape.*—Elliptical.

*Base shape.*—Acute to acuminate.

*Apex shape.*—Obtuse.

*Margin.*—Entire.

*Texture.*—Densely pubescent on both surfaces.

*Color of veins, upper and lower surfaces.*—RHS 144B.

*Petiole color.*—RHS 144C or RHS 145A.

*Petiole length.*—0.1-0.3 cm.

*Diameter of petiole.*—0.2 cm.

*Texture.*—Hirsute.

Stem:

*Color of stem.*—RHS 143C or RHS 146B, usually anthocyanin on the upper side of horizontal branches: resulting color more grey than RHS 177A.

*Length of stem.*—18-23 cm.

*Diameter.*—0.2-0.25 cm.

*Length of internodes.*—1.0-3.0 cm.

*Texture.*—Densely covered with soft hair of various length; glandular hairs.

Pedicel:

*Color of pedicel.*—RHS 146C, anthoycanin may occur near the base of the flower: the resulting color is RHS 147A or even as dark as RHS 177A.

*Length of pedicel.*—2.0-4.5 cm.

*Diameter of pedicel.*—0.1 cm.

*Texture of pedicel.*—Dense soft hair, glandular hairs.

Inflorescence:

*Type.*—Flowers solitary in upper leaf axils; flowers face mainly horizontally, 5 fused petals forming a funnel to salver shaped flower.

*Quantity of inflorescences per plant.*—10-20.

*Lastingness of individual flowers.*—About 7-9 days.

*Fragrance.*—None.

*Duration of flowering.*—Continuous flowering throughout the Summer.

Bud (just when starting to show color):

*Color.*—Approximately RHS 180C to RHS 180D upper part; lower part RHS 11C with dark veins of RHS 166A.

*Length.*—2.5-2.8 cm.

*Width.*—0.6-0.9 cm.

*Shape.*—Oblong.

Image inflorescence:

*Color upper surface.*—RHS 13A with RHS 28A stripes; or RHS 33A with fine lines of RHS 13A.

*Lower surface.*—RHS 39B with RHS 19A at center.

Mature inflorescence:

*Flower horizontal diameter.*—3.5-4.1 cm.

*Flower height (vertical).*—2.0-2.3 cm.

*Petal color, upper surface.*—RHS 13A with RHS 32B lines; or RHS 35A, with fine yellow stripes of RHS 16A; and with narrowish reddish ring of RHS 46B near the bottom portion of corolla opening.

*Lower surface.*—RHS 39B with RHS 19A at center.

*Petal apex shape.*—Truncate to slightly retuse.

*Petal margin.*—Entire.

*Waviness of petals.*—Very little.

*Petal lobation.*—Weak to medium.

*Petal texture.*—Papillose and glabrous on the upper side, short hair along the veins of the under side.

*Corolla, tube color outside, upper side.*—RHS 15D with RHS 166A veins.

*Underside.*—RHS 24C or RHS 22C, with fine middle lines of RHS N199A to RHS 199B.

*Corolla tube color inside.*—RHS 13A; fine RHS 165A veins.

*Corolla tube length.*—1.6-1.9 cm.

Calyx:

*Number of sepals.*—5.

*Color of sepals, upper surface.*—RHS 137A, slightly lighter basally.

*Color of sepals, outer/lower surface.*—RHS 137C, slightly lighter basally.

*Length of sepals.*—1.4-1.6 cm.

*Width of sepals.*—0.4-0.5 cm.

*Sepal shape.*—Lanceolate.

*Apex shape.*—Obtuse.

*Margins.*—Entire.

*Texture.*—Both surfaces densely covered with hairs.

Reproductive organs:

*Pistil.*—1.

*Pistil length.*—1.4 cm.

*Style color.*—RHS 145A.

*Style length.*—1.0-1.2 cm.

*Stigma color.*—RHS 144A.

*Number of stamens.*—5.

*Color of filaments.*—RHS 150D to RHS 155A.

*Length filaments.*—0.8-1.5 cm.

*Anther color.*—RHS 8A.
*Anther length.*—0.1 cm.
*Anther shape.*—Elliptical.
*Color of pollen.*—RHS 11B.
*Pollen amount.*—Moderate.
*Fertility/seed set.*—Not observed on this hybrid.

Disease/pest resistance: Disease/pest resistance has not been observed on this hybrid.

What is claimed is:

1. A new and distinct variety of *Calibrachoa* plant named 'Cal Orngise' substantially as illustrated and described herein.

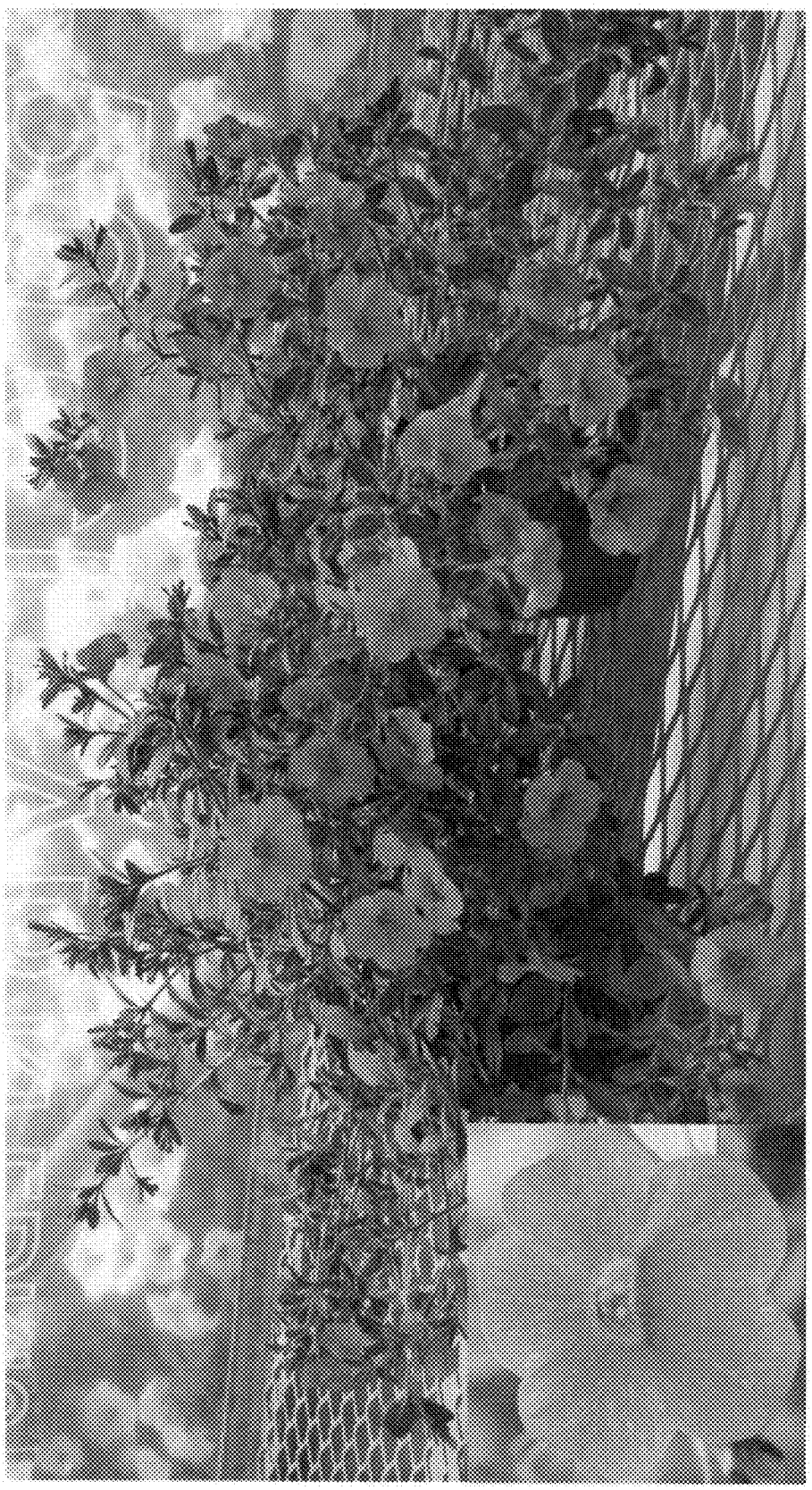

* * * * *